United States Patent [19]

Ohashi et al.

[11] 4,254,217
[45] Mar. 3, 1981

[54] HARDENER-INCORPORATED GELATIN COMPOSITION

[75] Inventors: Minoru Ohashi; Katsuaki Iwaosa, both of Nagaokakyo, Japan

[73] Assignee: Mitsubishi Paper Mills, Ltd., Tokyo, Japan

[21] Appl. No.: 49,049

[22] Filed: Jun. 15, 1979

[30] Foreign Application Priority Data

Jun. 19, 1978 [JP] Japan .................................. 53-74004
Aug. 25, 1978 [JP] Japan ................................ 53-103661

[51] Int. Cl.³ .......................... G03C 1/30; C09H 7/00
[52] U.S. Cl. .................................... 430/623; 430/523; 430/510; 430/961; 260/117; 106/125
[58] Field of Search ...................... 96/111; 260/117, 8; 106/125; 430/623, 523, 510, 961

[56] References Cited

U.S. PATENT DOCUMENTS

| | | | |
|---|---|---|---|
| 2,373,136 | 4/1945 | Hoover et al. | 528/239 |
| 2,629,659 | 2/1953 | Mueller | 96/111 |
| 2,732,316 | 1/1956 | July et al. | 96/111 |
| 3,207,604 | 9/1965 | Rauch et al. | 96/111 |
| 3,457,079 | 7/1969 | Koda et al. | 96/109 |
| 3,594,174 | 7/1971 | Haga et al. | 96/109 |
| 3,840,370 | 10/1974 | Dallon et al. | 96/111 |
| 4,104,302 | 8/1978 | Smith et al. | 96/111 |

Primary Examiner—Won H. Louie, Jr.
Attorney, Agent, or Firm—Cushman, Darby & Cushman

[57] ABSTRACT

There is provided a gelatin-hardening compound of the formula:

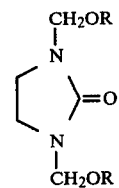

wherein R is a hydrogen atom, an alkyl group, a phenyl group, an acyl group represented by

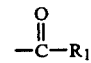

(where $R_1$ is an alkyl, phenyl, alkenyl, alkoxy or amino group), a carbamoyl group, an alkoxycarbonyl group or a sulfonyl group represented by

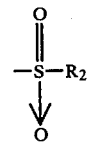

(where $R_2$ is an alkyl or phenyl group), which gives an improved mechanical strength to the gelatin-containing photographic layer.

12 Claims, No Drawings

HARDENER-INCORPORATED GELATIN COMPOSITION

This invention relates to a method of hardening gelatin by using a novel hardener, and more particularly it relates to a gelatin composition suited for hardening the gelatin film of photographic sensitive material.

Generally, photographic sensitive material is made by laminating various kinds of layers such as silver halide emulsion layer, filter layer, intermediate layer, protective layer, subbing layer, backing layer, ultraviolet absorbing layer and antihalation layer on a suitable support such as glass, paper, synthetic resin film, etc. Each of these composite layers is basically composed of gelatin and generally referred to as gelatin film.

The properties of such gelatin-based composite layers are naturally dependent, for the most part, on the properties of gelatin. The properties inherent to gelatin such as low melting point, excess water swelling tendency and poor mechanical strength are however the fatal defects for the composite layers of photographic sensitive material.

Attempts have been made for improving such gelatin properties by acting various kinds of hardener to gelatin to effect a cross-linking reaction with the functional groups such as amino, carboxyl and amide groups in the gelatin molecule. A number of compounds are known effective for hardening gelatin to increase water resistance, heat resistance and resistance to damage of the gelatin layer. Among such compounds are, for example, aldehyde compounds such as formaldehyde and glutaraldehyde; compounds having a reactive halogen such as disclosed in U.S. Pat. Nos. 3,288,775 and 2,732,303 and British Pat. Nos. 974,723 and 1,167,207; ketone compounds such as diacetal and cyclopentanedione; divinylsulfone, 5-acetyl-1,3-diacryloyl-hexahydro-1,3,5-triazine and other compounds having a reactive olefin such as shown in U.S. Pat. Nos. 3,635,718 and 3,332,763 and British Pat. No. 994,809; N-hydroxymethylphthalimide and other N-methylol compounds such as shown in U.S. Pat. Nos. 2,732,316 and 2,586,168; isocyanates such as disclosed in U.S. Pat. No. 3,103,437; aziridine compounds such as shown in U.S. Pat. Nos. 3,017,280 and 2,983,611; acid derivatives such as shown in U.S. Pat. Nos. 2,725,294 and 2,725,295; carbodiimide compounds such as shown in U.S. Pat. No. 3,100,704; epoxy compounds such as shown in U.S. Pat. No. 3,091,537; isooxazole compounds such as disclosed in U.S. Pat. Nos. 3,321,313 and 3,543,292; halogenocarboxyaldehydes such as mucochloric acid; dioxane derivatives such as dichlorodioxane, and other inorganic hardeners such as chromium alum, zirconium sulfate, chromium trichloride, etc. However, any of these known hardeners prove to be defective in some respect or other when used for the photographic sensitive material. For example, some of them are unsatisfactory in the hardening action and others cause "posthardening" (gradual change of hardening action with time), due to sluggish hardening reaction with gelatin. Some give an adverse effect (such as increased fogging, reduced sensitivity, softened tone, reduced maximum density, etc.) to the properties of the photographic sensitive material; some are deprived of their hardening action by other co-existing photographic additives or affect the effect of other additives (such as color-forming coupler in colorphotographic emulsion) or cause contamination; and some involve difficulties in synthesis of the compound used and can not be synthesized in mass quantity. Also, certain hardeners are unstable per se and have short shelf life.

Speed-up of treatment of photographic sensitive material is keenly requested recently, and efforts are being made for the operational and mechanical improvements in line with such tendency as well as the improvements of the treating solution best suited for such photographic sensitive material. For instance, in order to realize rapid penetration of the treating solution, attempt is being made to decrease the gelatin loading of the photographic sensitive material to make the layer thinner. However, this may cause not only deterioration of the film properties but also increased fogging. Therefore, with the spread of the high-temperature short-time treatment by use of automatic treating machines and strong treating solution, there is now a cry for the improved film quality, that is, high mechanical strength and ability to retain the normal photographic properties.

The primary object of this invention is to provide a novel hardener which is free of the said disadvantages of the conventional products and a method of hardening gelatin, particularly one suited for hardening the gelatin layer of the photographic sensitive material, by using such hardener.

Other objects and features of this invention will become apparent as the description of the invention proceeds hereinbelow.

These objects of this invention can be attained by using as gelatin hardener a compound represented by the following general formula:

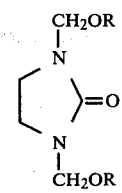

wherein R is a hydrogen atom, an alkyl group, a phenyl group, an acyl group represented by

(where $R_1$ is an alkyl, phenyl, alkenyl, alkoxy or amino group), a carbamoyl group, an alkoxy-carbonyl group or a sulfonyl group represented by

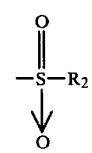

(where $R_2$ is an alkyl or phenyl group).

Listed below are the examples of the compounds used in this invention, such compounds being shown by way of the representations of $R_1$ and $R_2$ in the above-shown general formulae. The compounds of this invention, however, are not limited to these examples.

| Compound No. | R | R₁ | R₂ |
|---|---|---|---|
| (1) | H | — | — |
| (2) | —CH₃ | — | — |
| (3) | —C₂H₅ | — | — |
| (4) | —CH₂CH₂CH₃ | — | — |
| (5) | —CH(CH₃)₂ | — | — |
| (6) | —C₆H₅ (phenyl) | — | — |
| (7) | —C₆H₄—CO₂H (2-carboxyphenyl) | — | — |
| (8) | —C₆H₄—CO₂H (4-carboxyphenyl) | — | — |
| (9) | —C(=O)—R₁ | —CH₃ | — |
| (10) | —C(=O)—R₁ | —C₂H₅ | — |
| (11) | —C(=O)—R₁ | —CH₂CH₂CH₃ | — |
| (12) | —C(=O)—R₁ | —C₆H₅ (phenyl) | — |
| (13) | —C(=O)—R₁ | 2-carboxyphenyl | — |
| (14) | —C(=O)—R₁ | —CH=CH—CO₂H | — |
| (15) | —C(=O)—R₁ | —CH₂CH₂CO₂H | — |
| (16) | —C(=O)—R₁ | —OCH₃ | — |
| (17) | —C(=O)—R₁ | —OC₂H₅ | — |
| (18) | —C(=O)—R₁ | —O—C₆H₅ | — |
| (19) | —C(=O)—R₁ | —NH—CH₃ | — |
| (20) | —C(=O)—R₁ | —NH—C₂H₅ | — |
| (21) | —C(=O)—R₁ | —NH—C₆H₅ | — |
| (22) | —S(=O)(=O)—R₂ | — | —CH₃ |
| (23) | —S(=O)(=O)—R₂ | — | —C₂H₅ |
| (24) | —S(=O)(=O)—R₂ | — | —C₆H₅ |
| (25) | —S(=O)(=O)—R₂ | — | —C₆H₄—CH₃ |

Example of the synthetic processes for some typical compounds used in this invention are shown below.

SYNTHESIS EXAMPLE 1 (Compound (1))

This compound could be obtained by reacting ethyleneurea and paraformaldehyde in methanol according to the process shown in U.S. Pat. No. 2,373,136.

SYNTHESIS EXAMPLE 2 (Compound (2))

This compound could be obtained by reacting N,N'-bis(hydroxymethyl)ethyleneurea and methanol in a concentrated hydrochloric acid catalyst according to the process shown in U.S. Pat. No. 2,373,136.

SYNTHESIS EXAMPLE 3 (Compound (13))

14.6 gr of N,N'-bis(hydroxymethyl)ethyleneurea obtained in Synthesis Example 1 and 32.6 gr of phthalic anhydride were added 300 ml of dioxane, and the mixture was refluxed under heating for about 3 hours and then cooled. The crystals which separated out were then filtered out and recrystallized from about 200 ml of ethyl acetate to obtain 10 gr of the compound (13) with melting point of over 250° C.

Elemental analysis:
Calcd.: C, 57.1%; H, 4.10%; N, 6.33%. Found: C, 56.82%; H, 4.11%; N, 6.28%.

SYNTHESIS EXAMPLE 4 (Compound (9))

14.6 gr of N,N'-bis(hydroxymethyl)ethyleneurea and 18 gr of sodium acetate were suspended in 200 ml of dioxane, followed by addition of 30 ml of acetic anhydride, and the mixture was refluxed under heating for approximately 2 hours. After cooling, sodium acetate was filtered off and the filtrate was concentrated under reduced pressure and recrystallized from about 200 ml of ethyl acetate to obtain 18 gr of the compound (9).

Melting point: 139°–140° C.
Elemental analysis:
Cacld.: C, 46.95%; H, 6.13%; H, 12.17%. Found: C, 46.93%; H, 6.20%; N, 12.15%.

SYNTHESIS EXAMPLE 5 (Compound (17))

15.6 gr of N,N'-bis(hydroxymethyl)ethyleneurea and 35.6 gr of diethyl pyrocarbonate were dissolved in 200 ml of dioxane, and the mixture was refluxed under heating for approximately one hour. After cooling, the solvent was distilled off in vacuo and the residue was recrystallized from 70 ml of ethanol to obtain 5.3 gr of the compound (17) with melting point of 41°–44° C.

Elemental analysis:
Calcd.: C, 45.51%; H, 6.25%; N, 9.65%. Found: C, 45.29%; H, 6.31%; N, 9.65%.

SYNTHESIS EXAMPLE 6 (Compound (19))

14.6 gr of N,N'-bis(hydroxymethyl)ethyleneurea was dissolved in 200 ml of dioxane, and then methyl isocyanate was added dropwise in small portions thereto by a dropping funnel, and after completion of this dropwise addition, the mixture was refluxed under heating for approximately one hour. After cooling, the precipitated crystals were filtered out, washed well with dioxane and then dried in vacuo to obtain 19.5 gr of the compound (19). Melting point: 180°–181° C.

Elemental analysis:
Calcd.: C, 41.53%; H, 6.20%; N, 21.53%. Found: C, 41.51%; H, 6.28%; N, 21.58%.

In the gelatin hardening method of this invention gelatin and the compound may be contacted in any way for their reaction. Particularly, the reaction between said compounds and gelatin in the stratiform gelatin layer constituting a component element of the photographic sensitive material may be effectuated in various ways such as: adding a compound of this invention in a coating solution and then coating and drying same; adding in a coating solution a compound which has been preliminarily reacted with gelatin, and then coating and drying same; coating a coating solution containing said compound in the once coated layer to form a layer and then drying same; coating the component elements and then immersing same in a solution in which a compound of this invention has been dissolved, or immersing the coat in said compound-dissolved solution before or during the developing treatment.

In incorporating and hardener according to this invention in a coating solution for forming a gelatin film, the amount of such hardener to be added, although variable depending on the type, physical properties and photographic characteristics of the gelatin film to be formed, is usually 0.01 to 100%, preferably 0.1 to 10% by weight based on dry gelatin. Addition of the hardener may be made at any stage in the course of the preparation of the coating solution for forming gelatin film. However, in case of adding the hardener to a silver halide emulsion, it is preferably added at a point after second aging of the emulsion, more preferably just before coating.

The hardener according to this invention has no hygroscopicity and decomposability so that it suffers no change in quality even if it is stored for long time at room temperature. It is also well soluble in water and alcohol.

The hardener according to this invention, when acted on the gelatin film of a silver halide sensitive material, demonstrates an effective film hardening activity without inducing any undesirable effect such as fogging of the photographic emulsion nor affecting the normal photographic characteristics such as sensitivity. Also, because of little possibility of causing post-hardening with time, the hardener of this invention allows obtainment of a photographic sensitive material with stabilized quality and gives no adverse effect to the photographic emulsion in long-time preservation of the photographic sensitive material. It is further capable of providing the excellent film hardening property that can well withstand a high-temperature and high-speed treatment or an automatic treatment.

The hardener compositions according to this invention may be used either singly or in combination of two or more. They may be also used jointly with other known hardeners such as mentioned above.

It was also found that incorporation of at least one of the compounds of the following general formulae (I) to (IV) as assistant in a hardener-containing gelatin composition, especially in a gelatin containing photographic layer of the present invention can produce a stabilized hardening effect substantially free of the post-hardening phenomenon by using only the minimum amount of hardener required for reaching the desired saturated hardening level and by reaching such level in a short time.

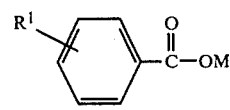

General formula (I)

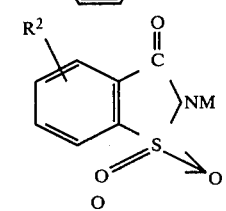

General formula (II)

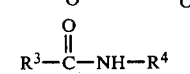

General formula (III)

General formula (IV)

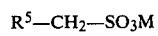

wherein $R^1$ and $R^2$ represent one or more substituents selected from the group consisting of hydrogen atom, an alkyl group (preferably substituted or unsubstituted alkyl group having 1 to 5 carbon atoms), a halogen atom, an alkoxy group (preferably one having 1 to 5 carbon atoms), a hydroxy group, a —$CO_2M$ group and a —$SO_3M$ group; $R^3$ and $R^4$ represent hydrogen atom, an alkyl group (preferably substituted or unsubstituted alkyl group having 1 to 5 carbon atoms), or an alkoxy group (preferably one having 1 to 5 carbon atoms), and $R^3$ and $R^4$ may constitute a closed ring together with the neighboring groups; $R^5$ represents a vinyl group (either substituted or unsubstituted) or a hydroxy group; and M is hydrogen atom or an alkali metal (preferably Na or K).

Shown below are typical examples of the compounds represented by the general formula (I) used in this invention:

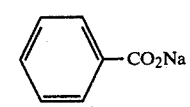

1-1

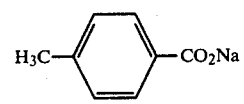

1-2

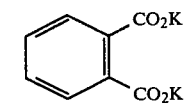

1-3

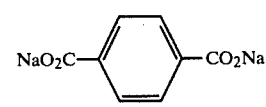

1-4

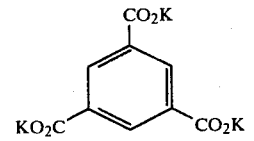

1-5

-continued

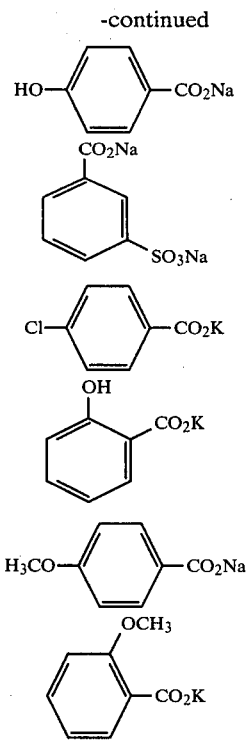

1-6
1-7
1-8
1-9
1-10
1-11

The followings are typical examples of the compounds of the general formula (II):

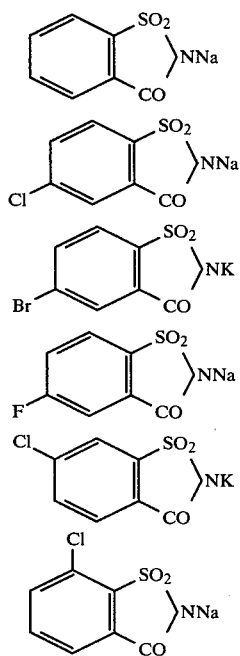

2-1
2-2
2-3
2-4
2-5
2-6

Listed below are typical examples of the compounds represented by the general formula (III):

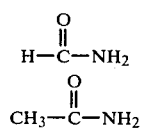

3-1
3-2

-continued $$H-\overset{\overset{O}{\|}}{C}-NH-CH_3$$ 3-3

$$CH_3-\overset{\overset{O}{\|}}{C}-NH-CH_3$$ 3-4

$$CH_3-\overset{\overset{O}{\|}}{C}-NH-C_2H_5$$ 3-5

$$CH_3-\overset{\overset{O}{\|}}{C}-NH-CH_2CH_2OH$$ 3-6

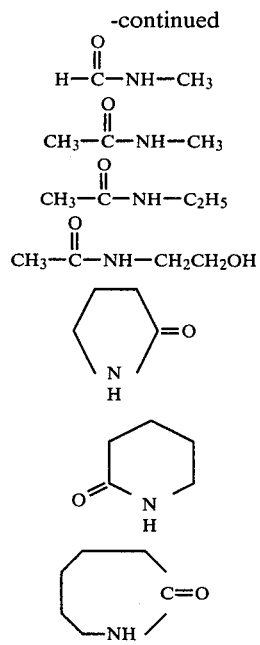

3-7
3-8
3-9

Among the typical examples of the compounds represented by the general formula (IV) are the following:

4-1    $CH_2=CH-CH_2-SO_3Na$ 4-2    $HO-CH_2-SO_3N_a$ 4-3    $CH_3\text{-}CH=CH-CH_2-SO_3 K$ 4—4    $H_5C_2\text{-}CH=CH\text{-}CH_2-SO_3 Na$ $$CH_2=\overset{\overset{CH_3}{|}}{C}-CH_2-SO_3K$$ 4-5

The above-exemplified compounds of the general formulae (I), (II) and (IV) form a salt with an alkali metal, but in case they are added to a silver halide photographic emulsion layer and/or its assistant layer, the corresponding free acid and its alkali metal salt may coexist depending on pH of said layer.

The silver halide photographic sensitive materials to which this invention can be applied include black-and-white, color and pseudo-color photographic materials, and they may be adapted to all types of uses such as printing, X-ray, radiation photography, etc., and may be used in any structural type such as negative type, positive type, diffusion transfer type, etc.

The gelatin to which the hardener of this invention is applied may be partly replaced, if so desired, with a cellulose derivative such as colloidal albumin, casein, carboxymethyl cellulose and hydroxyethyl cellulose, a saccharide derivative such as agar-agar, sodium alginate and starch derivatives, a synthetic hydrophilic colloid such as polyvinyl alcohol, poly-N-vinylpyrrolidone, polyacrylic acid copolymers, polyacrylamide or derivatives thereof, a partial hydrolyzate, etc. It may be also replaced with a so-called gelatin derivative, that is, a gelatin in which the amino, imino, hydroxy, carboxy or other like groups contained as functional groups in the molecule have been modified by a treatment with a reagent having one group reactable with said groups, or a graft polymer to which the molecular chains of other high-polymer material were bonded.

All types of silver halide such as silver bromide, silver iodide, silver bromochloride, silver bromochloroiodide, etc., may be used as sensitive component for the silver halide photographic sensitive material of this invention, and also such sensitive material can be subjected to various forms of chemical sensitization such as sensitization by a salt of noble metal such as ruthenium, palladium, rhodium, platinum, gold, etc., sulfur sensitization by a sulfur compound, selenium sensitization by a selenium compound, reduction sensitization by stonnous compound, polyamine, etc., or sensitization by a polyalkylene oxide compound. Said sensitive material may be also subjected to optital sensitization by a cyanine dye, merocyanine dye or the like. Further, it is possible to add in said sensitive material a variety of known photographic additives such as a stabilizer such as a triazole compound, azaindene compound, benzothiazolium compound, etc., a wetting agent such as dihydroxyalkane, an antistatics, an ultraviolet absorbing agent, a water-dispersable particulate high polymer obtained from an emulsion polymerization, saponin, polyethylene glycol lauryl ether, sodium dodecylbenzenesulfonate, and coating assistants such as fluorine type surface active agents shown in Japanese Patent Publication Nos. 9303/1972 and 43130/1973.

As support for the photographic sensitive material to which the hardening method of this invention can be applied, there may be used paper, laminate paper, and glass, cellulose acetate, cellulose nitrate, polyester, polyamide and polystyrene films and sheets.

The present invention is now described in further detail by way of the following examples.

EXAMPLE 1

A silver bromochloroiodide gelatin emulsion having the composition of 65.5 mol% silver bromide, 34.0% of silver chloride and 0.5 mol% of silver iodide and average particle size of 0.45 μm was prepared according to a neutral single jet method. After physical aging, the emulsion was desalted with water and added with gelatin and then with sodium thiosulfate to effect chemical sensitization, followed by further addition of a stabilizer and a surface active agent to finish the emulsion. The obtained gelatin-silver halide emulsion was divided into 30 portions. Of these total 30 portions, 25 portions (specimens 1 to 25) were added with the above-shown compounds 1 to 25, respectively, in an amount of 0.2 mmol per gram of gelatin. Of the remaining five portions which were purported as control, one was added with formaldehyde (Control A), another portion was added with a compound (Control B) represented by the formula:

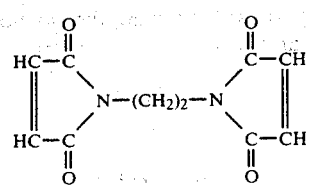

a compound (Control C) represented by the formula:

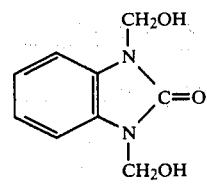

and a compound (Control D) represented by the formula:

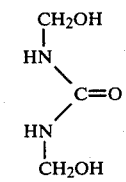

each in an amount of 0.2 mmol per gram of gelatin, and the remaining one portion was added with no hardener (Control E). Each of the thus obtained 30 emulsion specimens was applied on a polyethylene-coated photographic paper base at a coverage of 3.0 g/m² in terms of silver nitrate so that the gelatin deposit would be 5.0 g/m². After drying, each of the obtained specimens was heated at 40° C. for 5 days.

Each specimen was partly exposed through a stepped optical wedge, developed with a developing solution of the following composition at 20° C. for 120 seconds, fixed, washed with water, dried and then tested for the photographic properties.

| Developing solution: | |
|---|---|
| Water | 750 ml |
| Metol | 1.0 gr |
| Hydroquinone | 4.0 gr |
| Sodium sulfate | 15.0 gr |
| Sodium carbonate (monohydrate) | 26.7 gr |
| Potassium bromide | 0.7 gr |
| Water was added to make the total amount of the developing solution | 1,000 ml |

Another part of each specimen was not exposed and developed with the above deloping solution at 20° C. for 10 minutes and tested for fogging. The obtained results are shown in Table I below.

TABLE I

| Specimen No. | Compound | Gamma | Maximum density | Fog density |
|---|---|---|---|---|
| ① | (1) | 2.90 | 2.20 | 0.03 |
| ② | (2) | 2.80 | 2.10 | 0.03 |
| ③ | (3) | 2.80 | 2.15 | 0.02 |
| ④ | (4) | 2.70 | 2.00 | 0.03 |
| ⑤ | (5) | 2.90 | 2.20 | 0.04 |
| ⑥ | (6) | 2.85 | 2.18 | 0.03 |
| ⑦ | (7) | 2.90 | 2.20 | 0.03 |
| ⑧ | (8) | 2.90 | 2.20 | 0.04 |
| ⑨ | (9) | 2.80 | 2.20 | 0.04 |
| ⑩ | (10) | 2.70 | 2.10 | 0.02 |
| ⑪ | (11) | 2.75 | 2.10 | 0.02 |
| ⑫ | (12) | 2.60 | 2.00 | 0.02 |
| ⑬ | (13) | 2.70 | 2.10 | 0.02 |
| ⑭ | (14) | 2.85 | 2.20 | 0.02 |
| ⑮ | (15) | 2.80 | 2.20 | 0.02 |
| ⑯ | (16) | 2.90 | 2.20 | 0.03 |
| ⑰ | (17) | 2.80 | 2.18 | 0.03 |
| ⑱ | (18) | 2.70 | 2.10 | 0.03 |
| ⑲ | (19) | 2.75 | 2.15 | 0.02 |

TABLE I-continued

| Specimen No. | Compound | Gamma | Maximum density | Fog density |
|---|---|---|---|---|
| ⑳ | (20) | 2.60 | 2.00 | 0.02 |
| ㉑ | (21) | 2.65 | 2.10 | 0.02 |
| ㉒ | (22) | 2.90 | 2.20 | 0.03 |
| ㉓ | (23) | 2.90 | 2.20 | 0.03 |
| ㉔ | (24) | 2.80 | 2.18 | 0.02 |
| ㉕ | (25) | 2.70 | 2.10 | 0.02 |
| ㉖ | Control A | 2.40 | 1.90 | 0.06 |
| ㉗ | Control B | 2.30 | 1.80 | 0.03 |
| ㉘ | Control C | 2.70 | 2.05 | 0.03 |
| ㉙ | Control D | 2.55 | 1.90 | 0.03 |
| ㉚ | Control E | 3.00 | 2.30 | 0.04 |

It is noted from these results that the compounds of this invention are very limited in reduction of the maximum density and softening of tone (decrease of gamma value) and also low in fog density and give no adverse effect to the photographic properties.

EXAMPLE 2

Part of the 30 specimens obtained in Example 1 were immersed and heated in said developing solution and the emulsion film melting out temperature was measured to determine the melting point as a yardstick for the hardening degree. For determining the mechanical strength, the remaining specimens were immersed in said developing solution at 20° C. for 120 seconds and then a ball-pointed needle was placed on each specimen film surface vertically thereto and moved in contact with the specimen surface under load at the rate of 1 cm/sec. The load (g) which produced a scratch on the specimen film surface was measured and given as mechanical strength.

TABLE II

| Specimen No. | M.P. (°C.) | Mechanical strength (g) | Specimen No. | M.P. (°C.) | Mechanical strength (g) |
|---|---|---|---|---|---|
| ① | 90 | 160 | 16 | 92 | 195 |
| ② | 93 | 165 | 17 | 93 | 200 |
| ③ | 92 | 168 | 18 | 91 | 210 |
| ④ | 92 | 180 | 19 | 92 | 190 |
| ⑤ | 90 | 170 | 20 | 90 | 195 |
| ⑥ | 91 | 165 | 21 | 90 | 175 |
| ⑦ | 91 | 173 | 22 | 92 | 220 |
| ⑧ | 90 | 170 | 23 | 93 | 218 |
| ⑨ | 93 | 230 | 24 | 92 | 200 |
| ⑩ | 92 | 225 | 25 | 90 | 213 |
| ⑪ | 92 | 220 | 26 | 90 | 80 |
| ⑫ | 91 | 195 | 27 | 80 | 20 |
| ⑬ | 90 | 210 | 28 | 84 | 105 |
| ⑭ | 90 | 222 | 29 | 87 | 125 |
| ⑮ | 91 | 205 | 30 | 28 | 2.0 |

As apparent from Table II, the compounds of this invention showed a very excellent hardening action.

EXAMPLE 3

Specimens (Table III) were prepared in the same way as Example 1 except that the shown hardener (1) and a hardening assistant were added to the gelatin-silver halide emulsion of Example 1 in amounts of 0.2 mmol and 0.5 mmol, respectively, per gram of gelatin, and the obtained specimens were tested in the same way as said above except for heating at 40° C. for 4 days. The results are shown in Table III.

TABLE III

| Specimen No. | Hardener | Hardening assistant | Gamma | Max. density | Fog density |
|---|---|---|---|---|---|
| ㉛ | (1) | 1 - 1 | 2.90 | 2.22 | 0.03 |
| ㉜ | " | 1 - 2 | 2.92 | 2.21 | 0.03 |
| ㉝ | " | 1 - 3 | 2.93 | 2.23 | 0.02 |
| ㉞ | " | 1 - 9 | 2.89 | 2.21 | 0.03 |
| ㉟ | " | 2 - 1 | 2.91 | 2.22 | 0.02 |
| ㊱ | " | 3 - 1 | 2.90 | 2.21 | 0.03 |
| ㊲ | " | 3 - 2 | 2.89 | 2.19 | 0.03 |
| ㊳ | " | 3 - 3 | 2.90 | 2.18 | 0.02 |
| ㊴ | " | 3 - 4 | 2.90 | 2.20 | 0.03 |
| ㊵ | " | 3 - 6 | 2.90 | 2.21 | 0.03 |
| ㊶ | " | 3 - 9 | 2.87 | 2.22 | 0.03 |
| ㊷ | " | 4 - 1 | 2.88 | 2.23 | 0.03 |
| ㊸ | " | 4 - 2 | 2.91 | 2.21 | 0.03 |
| Control B | " | None | 2.90 | 2.20 | 0.03 |
| Control C-1 | None | 1 - 1 | 3.01 | 2.29 | 0.03 |
| Control C-2 | " | 2 - 1 | 3.02 | 3.32 | 0.02 |
| Control C-3 | None | 3 - 6 | 3.00 | 2.28 | 0.03 |
| Control C-4 | " | 3 - 9 | 2.99 | 2.27 | 0.02 |
| Control C-5 | " | 4 - 1 | 2.98 | 2.32 | 0.03 |

EXAMPLE 4

Part of the 19 specimens obtained in Example 3 were tested and tested for the mechanical strength according to the method of Example 2.

The remaining specimens were further subjected to additional 10-day heating (14 days in all) at 40° C. and similarly tested for the mechanical strength. The results are shown in Table IV.

TABLE IV

| | Mechanical strength (g) | |
|---|---|---|
| Specimen No. | Heated at 40° C. for 4 days | Heated at 40° C. for 14 days |
| ㉛ | 275 | 285 |
| ㉜ | 270 | 275 |
| ㉝ | 255 | 265 |
| ㉞ | 250 | 270 |
| ㉟ | 275 | 280 |
| ㊱ | 265 | 270 |
| ㊲ | 255 | 265 |
| ㊳ | 260 | 275 |
| ㊴ | 270 | 275 |
| ㊵ | 265 | 280 |
| ㊶ | 275 | 285 |
| ㊷ | 245 | 270 |
| ㊸ | 250 | 260 |
| Control B | 130 | 230 |
| Control C-1 | 3.0 | 3.0 |
| Control C-2 | 5.0 | 4.0 |
| Control C-3 | 3.0 | 4.0 |
| Control C-4 | 4.0 | 6.0 |
| Control C-5 | 3.0 | 5.0 |

What is claimed is:

1. A composition comprising gelatin and a hardener compound represented by the formula:

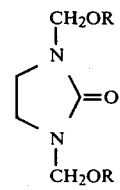

wherein R is a hydrogen atom, an alkyl group, a phenyl group, an acyl group represented by

                                    (5)

(where $R_1$ is an alkyl, phenyl, alkenyl, alkoxy or amino group), a carbamoyl group, an alkoxy carbonyl group or a sulfonyl group represented by

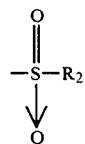

(where $R_2$ is an alkyl or phenyl group).

2. A gelatin-containing photographic layer comprising gelatin and a hardener compound represented by the formula:

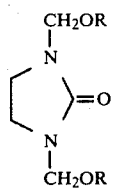

wherein R is a hydrogen atom, an alkyl group, a phenyl group, an acyl group represented by

(where $R_1$ is an alkyl, phenyl, alkenyl, alkoxy or amino group), a carbamoyl group, an alkoxycarbonyl or a sulfonyl group represented by

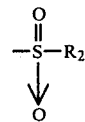

(where $R_2$ is an alkyl or phenyl group).

3. A gelatin-containing photographic layer of claim 2, wherein the said compound is at least one member selected from the group consisting of the compounds represented by the formulae:

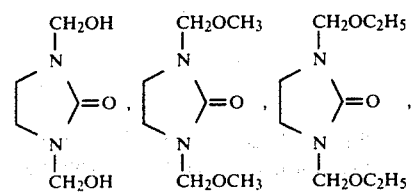

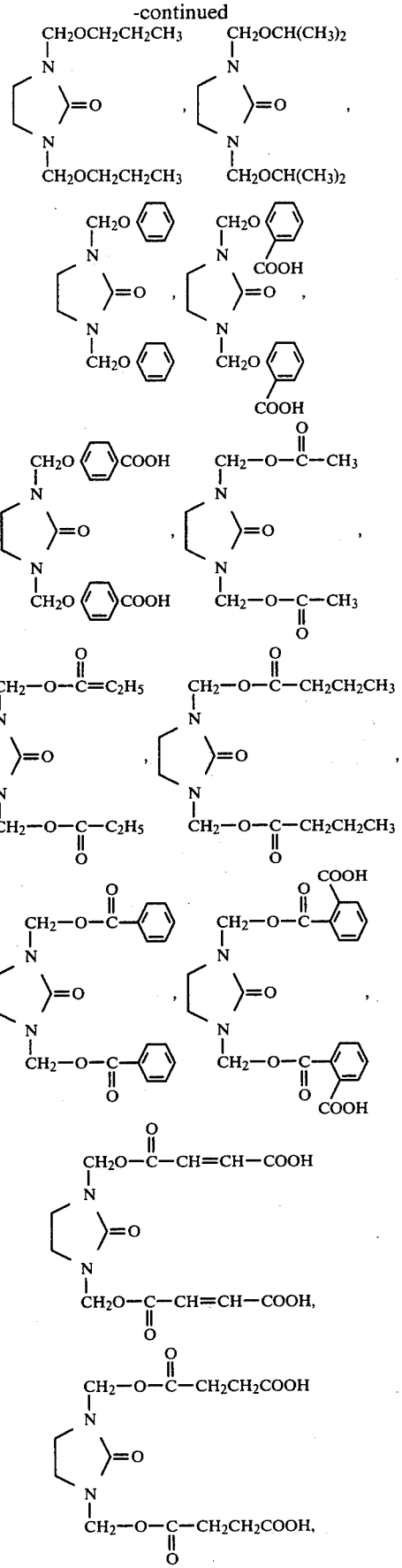

-continued
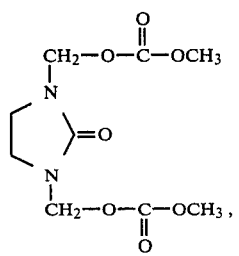
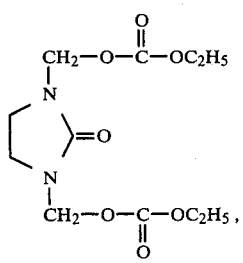
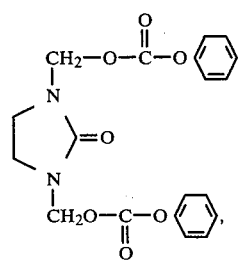
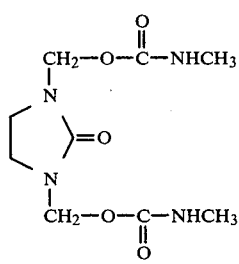
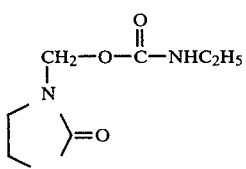
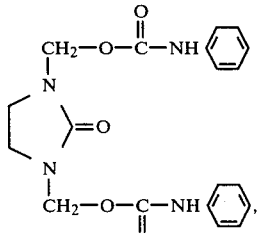
-continued
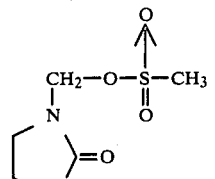
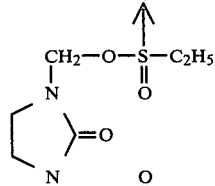
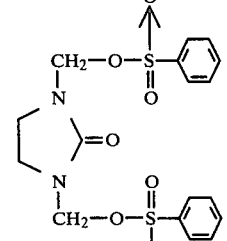
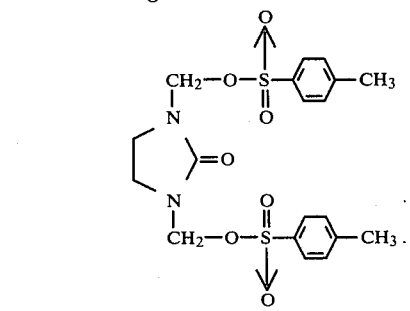
4. A gelatin-containing photographic layer of claim 2, characterized by containing as hardening assistant at least one compound selected from the group consisting of the compounds represented by the formulae:
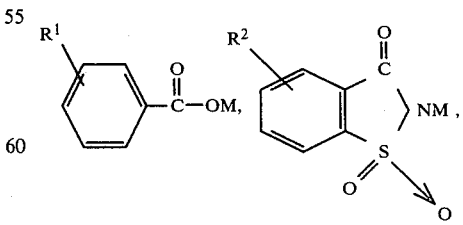
and $R^5$—$CH_2$—$SO_3M$ wherein $R^1$ and $R^2$ are respectively at least one substituent selected from a hydrogen atom, an alkyl group, a halogen atom, an alkoxy group, a hydroxy group, a —CO$_2$M group and a —SO$_3$M group; R$^3$ and R$^4$ are respectively hydrogen atom or an alkyl or alkoxy group, and R$^3$ and R$^4$ may form a closed ring together with the adjacent groups; R$^5$ is a vinyl or hydroxy group; and M is a hydrogen atom or an alkaline metal.

5. A composition of claim 1, wherein the amount of the hardener contained is 0.1 to 10% by weight based on the weight of gelatin.

6. A gelatin-containing photographic layer of claim 2, wherein the amount of the hardener contained is 0.1 to 10% by weight based on the weight of gelatin.

7. A photographic layer of claim 4, wherein the amount of the hardening assistant contained is 0.2 to 2 mmol per gram of gelatin.

8. A hardening method for a gelatin-containing photographic layer characterized in that a compound of the formula

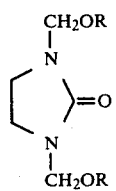

wherein R is a hydrogen atom, an alkyl group, a phenyl group, an acyl group represented by

(wherein R$_1$ is an alkyl, phenyl, alkenyl, alkoxy or amino group), a carbamoyl group, an alkoxycarbonyl group or a sulfonyl group represented by

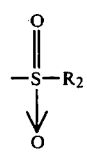

(where R$_2$ is an alkyl or phenyl group) is contained in at least one of the gelatin-incorporated composite layers and reacting said compound with the gelatin in said layer.

9. A process for hardening gelatin for a gelatin-containing photographic layer characterized by reacting gelatin with a hardener compound represented by the formula:

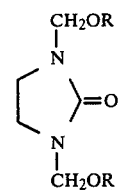

wherein R is a hydrogen atom, an alkyl group, a phenyl group, an acyl group represented by

(where R$_1$ is an alkyl, phenyl, alkenyl, alkoxy or amino group), a carbamoyl group, an alkoxy carbonyl group or a sulfonyl group represented by

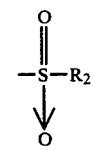

(where R$_2$ is an alkyl or phenyl group).

10. A process according to claim 9, wherein the reaction is carried out in the presence of at least one compound selected from the group consisting of the compounds represented by the formulae:

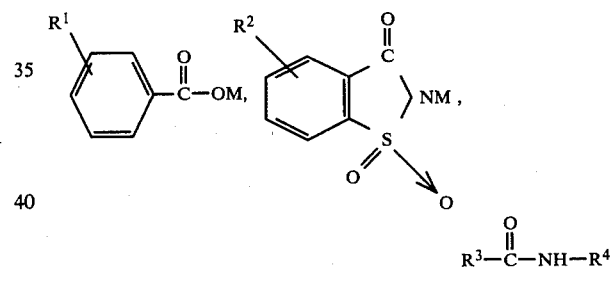

and R$^5$—CH$_2$—SO$_3$M wherein R$^1$ and R$^2$ are respectively one or more substituents selected from a hydrogen atom, an alkyl group, a halogen atom, an alkoxy group, a hydroxy group, a —CO$_2$M and a —SO$_3$M group; R$^3$ and R$^4$ are respectively a hydrogen atom or an alkyl or alkoxy group, and R$^3$ and R$^4$ may form a closed ring together with the adjacent groups; R$^5$ is a vinyl or hydroxy group; and M is hydrogen atom or an alkaline metal.

11. A composition according to claim 1 wherein R is the acyl group

12. A composition according to claim 1 wherein R is the sulfonyl group

* * * * *